United States Patent
Schall et al.

(10) Patent No.: US 10,045,810 B2
(45) Date of Patent: Aug. 14, 2018

(54) HIGH FREQUENCY SURGICAL GENERATOR COMPRISING AN ADDITIONAL TRANSFORMER

(75) Inventors: Heiko Schall, Nürtingen (DE); Erich Werner, Wannweil (DE); Marc Kegreiss, Rottenburg am Neckar (DE); Jürgen Beller, Gomaringen (DE)

(73) Assignee: ERBE ELEKTROMEDIZIN GMBH, Tuebingen (DE)

( * ) Notice: Subject to any disclaimer, the term of this patent is extended or adjusted under 35 U.S.C. 154(b) by 1205 days.

(21) Appl. No.: 13/256,162

(22) PCT Filed: Feb. 25, 2010

(86) PCT No.: PCT/EP2010/001178
§ 371 (c)(1),
(2), (4) Date: Nov. 1, 2011

(87) PCT Pub. No.: WO2010/102725
PCT Pub. Date: Sep. 16, 2010

(65) Prior Publication Data
US 2012/0041435 A1    Feb. 16, 2012

(30) Foreign Application Priority Data
Mar. 11, 2009    (DE) .......... 10 2009 012 600

(51) Int. Cl.
*A61B 18/12*    (2006.01)
*A61B 18/00*    (2006.01)

(52) U.S. Cl.
CPC ............ *A61B 18/1206* (2013.01); *A61B 2018/00642* (2013.01); *A61B 2018/00702* (2013.01);
(Continued)

(58) Field of Classification Search
CPC ...... A61B 18/1206; A61B 2018/00702; A61B 2018/00827; A61B 2018/00779;
(Continued)

(56) References Cited

U.S. PATENT DOCUMENTS 2,002,119 A    5/1935    Maxson
3,980,085 A    9/1976    Ikuno
(Continued)

FOREIGN PATENT DOCUMENTS

CA    1005123 A1    2/1977
CN    1308510 A    8/2001
(Continued)

*Primary Examiner* — Christopher D Koharski
*Assistant Examiner* — Pamela M Bays
(74) *Attorney, Agent, or Firm* — Blank Rome LLP

(57) ABSTRACT

An HF surgical appliance comprising an HF generator having an output circuit, which contains an output transformer and has an output impedance. Output terminals, to which an HF surgical instrument can be connected, are provided, said instrument supplying a high-frequency current with a specific frequency into tissue to treat the same. An additional output circuit containing an additional transformer, which is connected between the output circuit and the output terminals to reduce the output impedance is also provided. In this way, the HF surgical appliance can be operated with a high power output even on loads having low impedance.

7 Claims, 1 Drawing Sheet

(52) U.S. Cl.
  CPC ............... *A61B 2018/00755* (2013.01); *A61B 2018/00875* (2013.01); *A61B 2018/1286* (2013.01)

(58) Field of Classification Search
  CPC ........... A61B 2018/00642; A61B 2018/00755; A61B 2018/1286
  USPC .................................................... 606/34, 41
  See application file for complete search history.

(56) References Cited

U.S. PATENT DOCUMENTS

| | | | | |
|---|---|---|---|---|
| 4,473,075 A | * | 9/1984 | Rexroth | ................. A61B 18/12 606/37 |
| 4,626,728 A | * | 12/1986 | Flachenecker et al. | . 310/316.01 |
| 4,944,302 A | * | 7/1990 | Hernandez | ............... A61N 1/40 601/15 |
| 5,168,870 A | * | 12/1992 | Kohl | ................................ 607/5 |
| 5,647,869 A | * | 7/1997 | Goble | .................... A61B 18/12 606/37 |
| 6,019,775 A | * | 2/2000 | Sakurai | .......... A61B 17/320068 433/119 |
| 6,177,849 B1 | * | 1/2001 | Barsellotti et al. | ........... 333/177 |
| 6,508,815 B1 | | 1/2003 | Strul et al. | |
| 2002/0118000 A1 | | 8/2002 | Xu et al. | |
| 2005/0113820 A1 | * | 5/2005 | Goble | ................ A61B 18/1206 606/34 |
| 2008/0071260 A1 | * | 3/2008 | Shores | ............................ 606/34 |
| 2008/0103495 A1 | * | 5/2008 | Mihori | ............... A61B 18/1206 606/38 |
| 2009/0036939 A1 | | 2/2009 | Singh et al. | |

FOREIGN PATENT DOCUMENTS

| | | |
|---|---|---|
| DE | 25 26 928 A1 | 12/1975 |
| DE | 695 19 405 T2 | 5/2001 |
| DE | 103 51 818 A1 | 6/2005 |
| EP | 1 728 481 A1 | 12/2006 |
| JP | S49-19685 A | 2/1974 |
| JP | S50-161082 A | 12/1975 |
| JP | 2003-526385 A | 9/2003 |
| WO | WO 99/58070 A2 | 11/1999 |

* cited by examiner

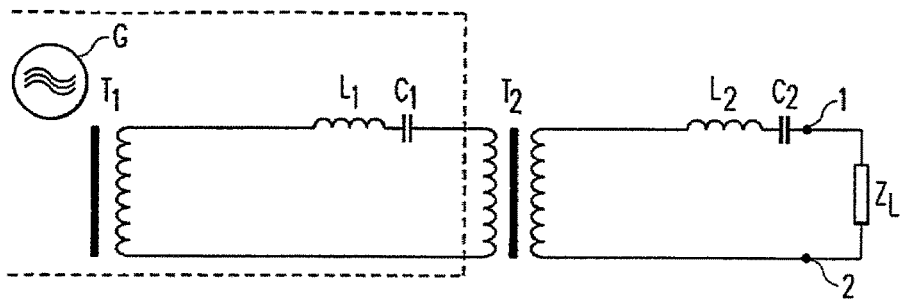
Fig. 1
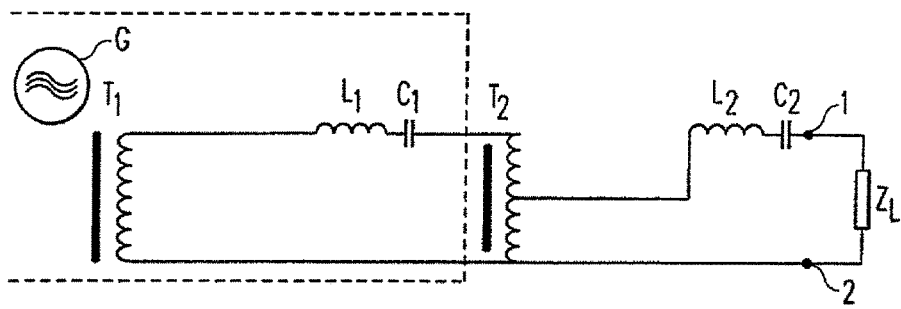
Fig. 2
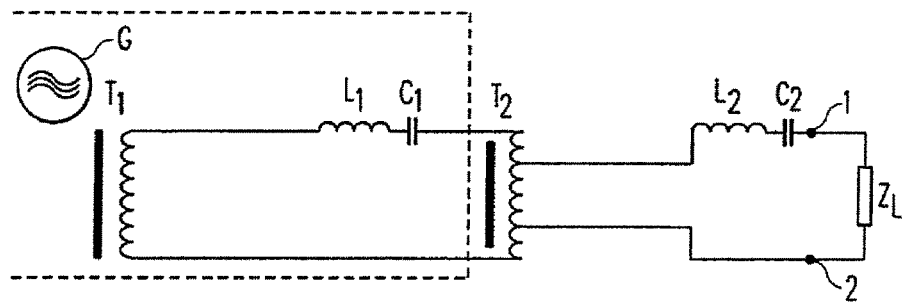
Fig. 3
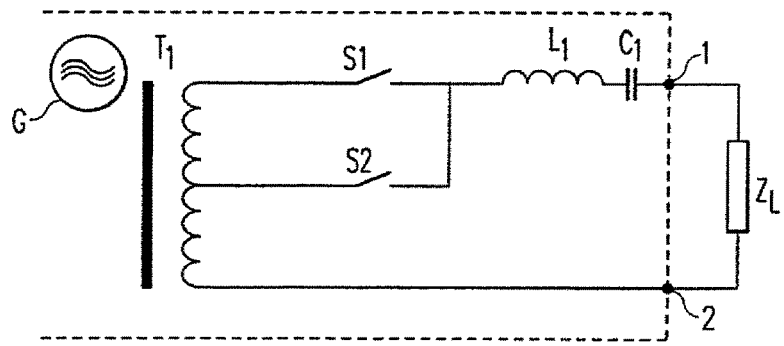
PRIOR ART    Fig. 4

HIGH FREQUENCY SURGICAL GENERATOR COMPRISING AN ADDITIONAL TRANSFORMER

FIELD OF THE INVENTION

The invention relates to an HF surgical appliance having an HF generator and an additional transformer.

BACKGROUND

HF surgical appliances are known for a plurality of possible applications. With some of these possible applications, the load impedance lies between 0.1 and 1 kΩ, with other possible applications, the load impedance can be even lower. In particular, when a transurethral resection of the prostate (TUR) is to be performed with a bipolar instrument with a highly conductive irrigant fluid (NaCl 0.9%), the load impedance is only about 20Ω.

To be able to perform a load adaptation with a conventional HF surgical appliance, as shown in FIG. 4, a generator G is provided in the HF surgical appliance (indicated in FIG. 4 with a broken line); the generator G comprises an output transformer $T_1$ that supplies, via an inductance $L_1$ and a capacitance $C_1$, which together form a resonant circuit, output terminals 1, 2, on which the load resistor $Z_L$ is suspended. With a high-resistance load, a first switch S1 is closed so that the entire secondary winding of the transformer $T_1$ is coupled to the load resistor $Z_L$ via the resonant circuit. In the case of a low load impedance $Z_L$, only a part of the secondary winding of the transformer $T_1$ is coupled via the switch S2 to the load $Z_L$. In this case, although an improvement of the adaptation conditions of the impedances is ensured, the transformer $T_1$ has to be provided with a winding that has a larger wire cross section than the rest of the windings, or has an even larger overall wire cross section, to tap the switch S2. This is obviously a drawback. Furthermore, the adaptation of the resonant circuit, which has to take place in dependence on the generator frequency and the load $Z_L$, no longer takes place in one or the other switch position.

SUMMARY

It is an object of the embodiments of the invention to provide an HF surgical appliance of the type discussed above in which adaptation to low loads is also enabled.

This object is achieved by an HF surgical appliance comprising an HF generator having an output circuit, which contains an output transformer, has an output impedance and comprises output terminals to which an HF surgical instrument for supplying a high-frequency current with a specific frequency into tissue for treating the same can be connected. An additional output circuit, which contains an additional transformer connected between the output circuit and the output terminals to reduce the output impedance is also provided.

The additional output circuit can either be embodied as an external additional appliance or mounted in the HF surgical appliance. This ensures, in a simple manner, that a conventional surgical appliance can be used for special purposes (with a low-resistance load) with a little amount of work.

Preferably, the additional transformer is embodied as an autotransformer so that the galvanic separation is provided by the transformer provided in the HF surgical appliances. This additional transformer comprises an asymmetric or, preferably, a symmetrical winding.

The additional transformer preferably has a small air gap, particularly no air gap. This enables the adaptation to be optimized. In addition, the additional transformer is preferably a low-scattering transformer. Moreover, the inductance of the additional transformer is preferably more than 1 mH.

The additional output circuit also comprises a capacitor between the additional transformer and the output terminals. It is preferable, however, that a resonant circuit having a resonant frequency above the specific frequency of the generator be provided. This further improves the adaptation to the load.

BRIEF DESCRIPTION OF THE DRAWINGS

Exemplary embodiments of the invention will be described in more detail with reference to drawings, in which:

FIG. 1 is a circuit diagram of a first embodiment of the invention;

FIG. 2 is a circuit diagram of a second embodiment of the invention;

FIG. 3 is a circuit diagram of a third embodiment of the invention; and

FIG. 4 is a circuit diagram of an arrangement that only works with the output transformer of the HF surgical appliance.

DETAILED DESCRIPTION

In the following description, the same reference numbers are used to refer to the same parts and parts with the same function.

FIG. 1 shows an HF surgical appliance that comprises a generator G comprising an output transformer $T_1$ and a resonant circuit $L_1$, $C_1$ as an output circuit. This arrangement is coupled to an additional transformer $T_2$ that has more turns in the primary winding than in the secondary winding. The additional transformer $T_2$ is connected, via another resonant circuit $L_2$, $C_2$, to output terminals 1, 2 to which a load $Z_L$ is applied. The additional transformer $T_2$ reduces the internal resistance of the overall arrangement in such a way that a substantially adaptation to the load impedance $Z_L$ takes place. The additional resonant circuit $L_2$, $C_2$ is designed so that adaptation, taking into account the output frequency of the generator G and the load $Z_L$, takes place.

The embodiment shown in FIG. 2 differs from that shown in FIG. 1 in that the additional transformer $T_2$ is embodied as an autotransformer. The embodiment in FIG. 3 differs from that shown in FIG. 2 in that this autotransformer $T_2$ has a symmetrical tap for coupling the load $Z_L$ (via the resonant circuit $L_2$, $C_2$).

The invention claimed is:

1. An HF surgical appliance comprising:
   an HF generator having an output circuit, said output circuit comprising an output transformer, an output impedance and output terminals, to which an HF surgical instrument can be connected, the HF surgical instrument configured to supply a high-frequency current with a specific frequency used for treating tissue; and
   an additional output circuit containing an additional transformer that is connected between the output circuit and the output terminals to reduce the output impedance, wherein
   the additional transformer has more turns in a primary winding than in a secondary winding in order to reduce the output impedance;

the additional output circuit comprises a resonant circuit whose resonance frequency is higher than the specific frequency of the HF generator, and wherein the additional output circuit is embodied as an external additional appliance outside the HF surgical appliance.

2. The HF surgical appliance of claim 1, wherein the additional transformer comprises a small air gap.

3. The HF surgical appliance of claim 1, wherein the additional transformer comprises no air gap.

4. The HF surgical appliance of claim 1, wherein the additional transformer is a low-scattering transformer.

5. The HF surgical appliance of claim 1, wherein the additional transformer has an inductance of more than 1 mH.

6. The HF surgical appliance of claim 1, wherein the additional output circuit comprises a capacitance between the additional transformer and the output terminals.

7. An HF surgical appliance comprising:

an HF generator having an output circuit, said output circuit comprising an output transformer, an output impedance and output terminals, to which an HF surgical instrument can be connected, the HF surgical instrument configured to supply a high-frequency current with a specific frequency used for treating tissue; and an additional output circuit containing an additional transformer that is connected between the output circuit and the output terminals to reduce the output impedance, wherein the additional transformer has more turns in a primary winding than in a secondary winding in order to reduce the output impedance;

the additional output circuit comprises a resonant circuit whose resonance frequency is higher than the specific frequency of the HF generator, and the additional output circuit is mounted in the HF-surgical appliance.

* * * * *